United States Patent
Fujino et al.

(10) Patent No.: US 9,974,727 B2
(45) Date of Patent: May 22, 2018

(54) HAIR GROWTH AND HAIR RESTORATION MATERIAL

(71) Applicant: INSTITUTE OF RHEOLOGICAL FUNCTION OF FOOD CO., LTD., Fukuoka (JP)

(72) Inventors: Takehiko Fujino, Fukuoka (JP); Osami Nada, Koga (JP); Yoshitaka Nadachi, Tokyo (JP); Gunki Funatsu, Fukuoka (JP)

(73) Assignee: Institute of Rheological Function of Food Co., Ltd., Fukuoka (JP)

( * ) Notice: Subject to any disclaimer, the term of this patent is extended or adjusted under 35 U.S.C. 154(b) by 121 days.

(21) Appl. No.: 15/065,645

(22) Filed: Mar. 9, 2016

(65) Prior Publication Data
US 2016/0184207 A1   Jun. 30, 2016

Related U.S. Application Data

(63) Continuation of application No. 14/123,074, filed as application No. PCT/JP2012/003545 on May 30, 2012, now abandoned.

(30) Foreign Application Priority Data

May 31, 2011 (JP) ................. 2011-121662

(51) Int. Cl.
| | | |
|---|---|---|
| *A01N 43/04* | (2006.01) | |
| *A61K 31/70* | (2006.01) | |
| *A61K 8/63* | (2006.01) | |
| *A61Q 7/00* | (2006.01) | |
| *A61K 31/704* | (2006.01) | |
| *A61K 8/60* | (2006.01) | |
| *A61K 31/7028* | (2006.01) | |
| *A61K 31/7032* | (2006.01) | |
| *A61K 31/7034* | (2006.01) | |

(52) U.S. Cl.
CPC ............... *A61K 8/63* (2013.01); *A61K 8/602* (2013.01); *A61K 31/704* (2013.01); *A61Q 7/00* (2013.01); *A61K 31/7028* (2013.01); *A61K 31/7032* (2013.01); *A61K 31/7034* (2013.01); *A61K 2800/40* (2013.01)

(58) Field of Classification Search
None
See application file for complete search history.

(56) References Cited

U.S. PATENT DOCUMENTS

| | | | |
|---|---|---|---|
| 8,178,136 B2 * | 5/2012 | Giuliani | A61K 8/97 424/725 |
| 2014/0142053 A1 * | 5/2014 | Ismail | A61K 31/704 514/25 |

FOREIGN PATENT DOCUMENTS

| | | |
|---|---|---|
| JP | 63-238010 A | 10/1988 |
| JP | 04-005219 A | 1/1992 |
| JP | 05-025023 A | 2/1993 |
| JP | 07-109295 A | 4/1995 |
| JP | 07-191835 A | 4/1995 |
| JP | 10-017439 A | 1/1998 |
| JP | 2003-221315 A | 8/2003 |
| JP | 2006-151940 A | 6/2006 |
| JP | 2008-024628 A | 2/2008 |

OTHER PUBLICATIONS

Folmer Advances in Colloid and Interface Science (2003), vol. 103, pp. 99-119.*
International Search Report issued in PCT/JP2012/003545, dated Aug. 7, 2012, with English translation.
Tietz, A. et al., (1977) Steryl-Glucosides: A Group of Substances in Plants with Hormone-like Activity and Biphasic Dose Response Curve, Zeitschrift fuer Pflanzenphysiologie, Vol, 81, p. S57-67.
Ly, P.T.T. et al., (2008) Cholesteryl Glucoside Stimulates Activation of Protein Kinase B/Akt in the Motor Neuron-Derived NSC34 Cell Line, Neurobiology of Lipids, vol. 7, No. 4.

* cited by examiner

*Primary Examiner* — Patrick T Lewis
(74) *Attorney, Agent, or Firm* — McDermott Will & Emery LLP

(57) ABSTRACT

Provided is a novel hair growth and hair restoration material having excellent efficacy in hair growth and hair restoration for both men and women, even when the components thereof are at ultra-dilute concentrations; the hair growth and hair restoration material being characterized in containing a sterol glucopyranoside, preferably a cholesteryl glucopyranoside, represented by general formula (I). (In the formula, Z represents a sterol residue from which the hydroxyl group attached to the 3-position of a cyclopentanohydrophenanthrene ring has been removed.)

5 Claims, 5 Drawing Sheets

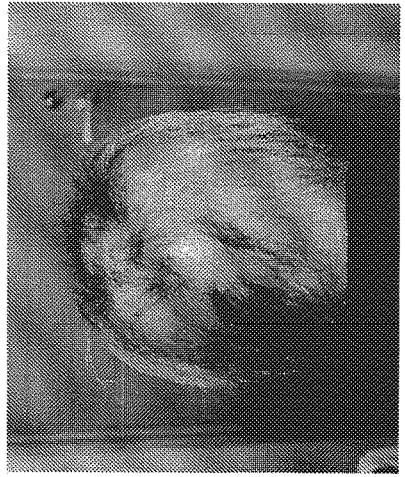 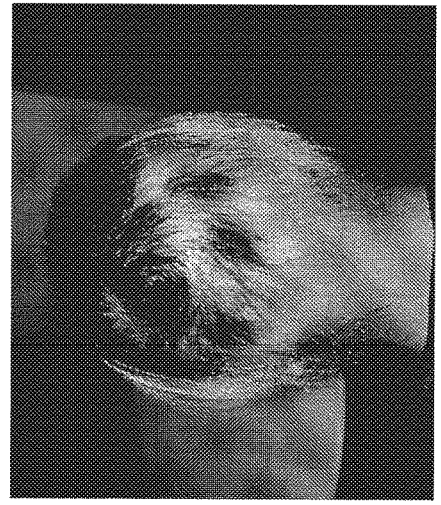
Fig.5 Back of Head Before Application / Back of Head After Application

HAIR GROWTH AND HAIR RESTORATION MATERIAL

RELATED APPLICATIONS

This application is a continuation of U.S. patent application Ser. No. 14/123,074, filed Jun. 9, 2014, which is the U.S. National Phase under 35 U.S.C. § 371 of International Application No. PCT/JP2012/003545, filed on May 30, 2012, which in turn claims the benefit of Japanese Application No. 2011-121662, filed on May 31, 2011, the disclosures of which are incorporated by reference herein.

TECHNICAL FIELD

The present invention relates to a novel hair growth and hair restoration material. More particularly, the invention relates to a hair growth and hair restoration material which contains, as an active ingredient, a steryl glucopyranoside, preferably a cholesteryl glucopyranoside, and which exhibits excellent hair growth and hair restoration effects even when the concentration of the component is extremely dilute at $10^{-13}$ or $10^{-12}$ g/mL.

BACKGROUND ART

The causes of alopecia are considered to be related to disturbances in hormone balance, disturbances of circulation of capillaries surrounding hair papillae and hair follicles, excessive hyperfunction of sebaceous glands or deficient sebum secretion, accumulation of stress, declines in immune function, hypofunction in hair matrix cells, abnormal activity of various enzymes involved in hair growth, excessive dandruff formation (abnormal sebum secretion/proliferation of scalp bacteria), scalp tension, excessive dryness, and the like.

In order to prevent such hair loss, stimulate hair growth, and promote hair growth (new hair growth), the following measures are believed to be effective:

(1) promotion of local blood circulation and metabolism
(2) promotion of proliferation of hair follicle cells
(3) Prevention of hair loss caused by androgens and suppression of sebum secretion
(4) Preservation of scalp environment Healthy human hair is shed and replaced by new growth at a cycle of about 5 or 6 years.

This cycle is classified into three phases: an "anagen" in which the hair follicle is formed and hair grows, a "catagen" in which growth regresses, and a "telogen" in which growth stops.

In male-pattern hair loss, it has been known that the hair cycle gradually shortens, the anagen phase becomes shortened, and as a result, thick, long terminal hair transforms into lanugo-like vellus hair.

By promoting blood flow in the scalp, oxygen and nutrients are supplied to hair follicles via capillaries mainly in hair papillae and in the periphery of mesenchymal cells surrounding hair follicles, and then cause epithelial cells, such as hair matrix cells, to proliferate smoothly, which is thus believed to be effective, in particular, in the anagen phase. However, a detailed mechanism thereof has not been clarified.

In addition to blood circulation promotion, vasodilation, and energy supply, many studies have been conducted on drugs for balancing hormones, which have hair loss suppression and hair growth promotion effects from the standpoint of androgen suppression.

Although the hair loss mechanism has not been sufficiently elucidated, the development of hair restoring drugs is in progress from this viewpoint.

Additionally, although not yet in the drug development stage, studies have been conducted as to the effects of cell growth factors and substances, such as neurotransmitters, on cells constituting hair follicles, as to association of apoptosis-related substances, hair follicle-inducing factors, angiogenesis factors, and the like with the hair cycle, as to hair growth promotion thereof, prolongation of the anagen phase, and the like.

It has been reported that, even in male-pattern hair loss, a slight inflammation is caused around hair follicles although not so severe as that seen in alopecia areata. Studies are being conducted on cytokines in association with male-pattern hair loss.

Fewer studies have been conducted on thinning hair in women than on thinning hair in men.

However, in recent years, the number of women worrying about thinning hair has been increasing.

This is said to be caused by stress resulting from women's social advancement and the like.

In male-pattern hair loss, it is known that since the hair follicle growth phase shortens, the number of immature hair follicles increases, resulting in an increase in lanugo-like hair.

On the other hand, in women, since the anagen ratio does not substantially change, the reason for thinning hair is believed to be transformation of terminal hair into fine hair, rather than an increase of lanugo-like hair.

That is, it is believed to be possible to grow thick hair by thickening hair follicles and moreover by actively proliferating hair follicle cells.

It is known that, the hair root of anagen hair is embedded deep into the fatty layer under the dermis, and when the anagen phase lasting about 5 to 6 years ends, the hair root gradually shortens to about a half through the catagen phase to the telogen phase.

When a new anagen phase is initiated, the hair root is gradually embedded deep into the fatty layer again, and new hair growth starts.

It has been confirmed that, during the time when the anagen hair follicle grows, many positive cells are observed in hair matrix cells around the hair papilla and root sheath cells around the hair shaft.

Consequently, under the assumption that it is important for improving women's thinning hair to promote proliferation of root sheath cells, research has been conducted on the development of drugs for promoting cell proliferation in cell culture systems.

On the other hand, for example, as seen in Japanese Unexamined Patent Application Publication No. 4-5219 (Patent document 1) and Japanese Unexamined Patent Application Publication No, 5-25023 (Patent document 2), research has been conducted on hair growth and hair restoration components containing a steroid glycoside and/or a triterpenoid glycoside.

Furthermore, for example, Japanese Unexamined Patent Application Publication No. 7-109295 (Patent document 3) discloses a hair growth and hair restoration material containing, as an active ingredient, a stigmasterol glycoside which is a type of steroid glycoside.

CITATION LIST

Patent Documents

Patent document 1: Japanese Unexamined Patent Application Publication No. 4-5219

Patent document 2: Japanese Unexamined Patent Application Publication No. 5-25023

Patent document 3: Japanese Unexamined Patent Application Publication No. 7-109295

SUMMARY OF INVENTION

Technical Problem

The stigmasterol glycoside described in the Patent Literature 3 is stigmasterol maltoside, maltotrioside, maltotetraoside, or maltopentaoside.

The content of the stigmasterol glycoside in the hair restoration material is 0.0005% to 5% by mass (1% by mass in Examples), which is a usual concentration as a hair restoration material.

The stigmasterol is widely distributed in the plant kingdom, such as in soybean oil, coconut oil, and cotton seeds, and the cholesterol is a sterol that is widely distributed in the animal kingdom.

As described above, in anticipation of hair growth and hair restoration effects of the triterpenoid glycoside and the steroid glycoside, various attempts to realize these effects have been made. However, under actual circumstances, sufficient hair growth and hair restoration effects have not been obtained.

Under these circumstances it is an object of the present invention to provide a novel hair growth and hair restoration material which exhibits excellent hair growth and hair restoration effects for both men and women.

The present inventors have earlier developed a water-soluble keratin derivative prepared using, as a raw material, poultry feathers, and has found that the water-soluble keratin derivative is useful as a high energy wave absorber, a luminescent material, a weatherproofness improver, a water repellent, and the like.

As a result of further research on the water-soluble keratin derivative, it has been found that the keratin derivative has a hair growth effect on shaved mice, and it has been determined that the active ingredient effective for hair growth is a cholesteryl glucopyranoside.

More research has been conducted, and as a result, it has been found that steryl glucopyranosides other than the cholesteryl glucopyranoside also have hair growth and hair restoration effects and that excellent hair growth and hair restoration effects are exhibited surprisingly in an extremely dilute solution in a certain concentration range.

The present invention has been achieved on the basis of such findings.

Solution to Problem

That is, the invention according to claim 1 provides a hair growth and hair restoration material characterized by containing a steryl glucopyranoside represented by general formula (I).

(In the formula, Z represents a sterol residue from which the hydroxyl group attached to the 3-position of a cyclopentanohydrophenanthrene ring has been removed.)

Furthermore, the invention according to claim 2 provides the hair growth and hair restoration material according to claim 1, characterized in that the sterol residue in the general formula (I) is a cholesterol residue, a β-sitosterol residue, a stigmasterol residue, a campesterol residue, or a brassicasterol residue.

Furthermore, the invention according to claim 3 provides the hair growth and hair restoration material according to claim 1, characterized in that the steryl glucopyranoside is a cholesteryl glucopyranoside.

Furthermore, the invention according to claim 4 provides the hair growth and hair restoration material according to any one of claims 1 to 3, characterized in that the steryl glucopyranoside is a naturally occurring substance and/or a synthetic product.

Furthermore, the invention according to claim 5 provides the hair growth and hair restoration material according to claim 3, characterized in that the cholesteryl glucopyranoside is obtained from bird feathers.

Effects of Invention

The hair growth and hair restoration material according to the present invention contains, as an active ingredient, a steryl glucopyranoside, preferably a cholesteryl glucopyranoside, and exhibits excellent hair growth and hair restoration effects even at a dilute concentration.

BRIEF DESCRIPTION OF DRAWINGS

FIG. 5 includes photographs of a head, showing the results of a hair growth test on head hair of a 35-year-old male applied with FCG in Example 6 of the present invention.

DESCRIPTION OF EMBODIMENTS

Figure 1:
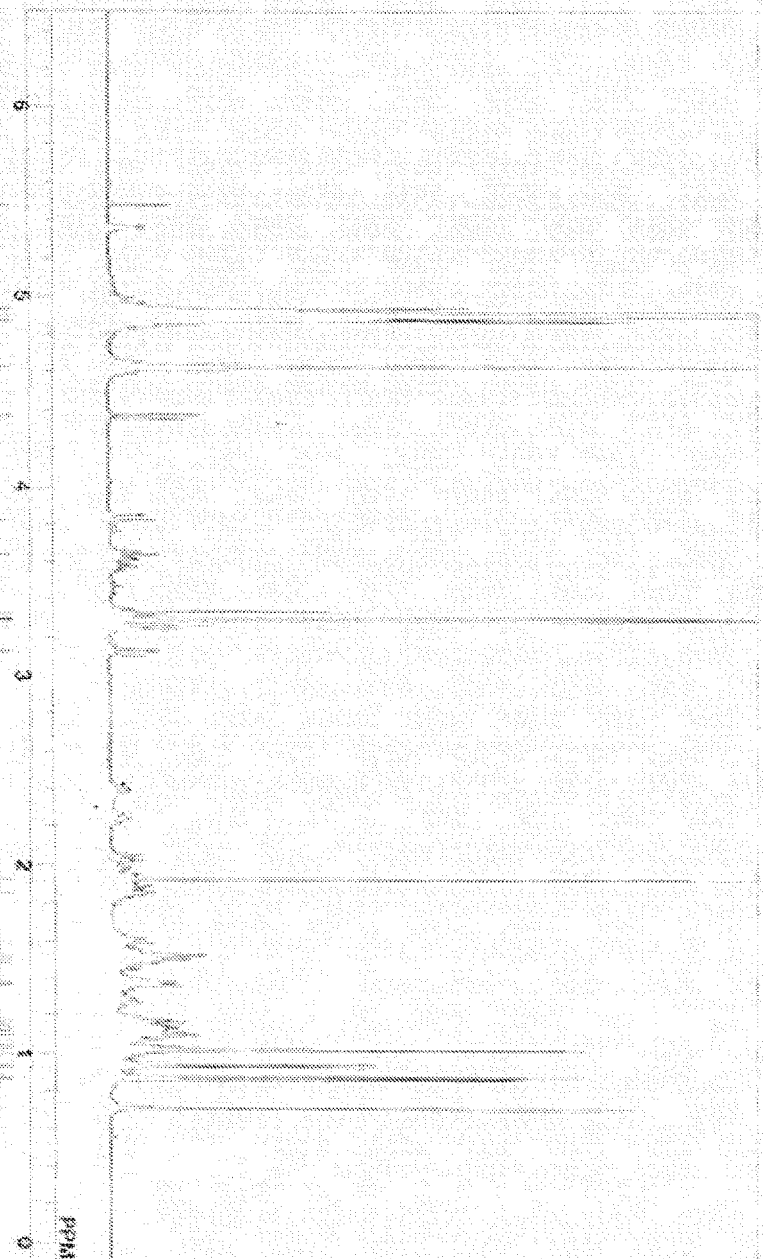
FIG. 1 is a $^1$H-NMR chart (500 MHz in $D_2O$) of cholesteryl-β-D-glucopyranoside (synthetic CG) obtained in Production Example 2-(3) (b).

A hair growth and hair restoration material according to the present invention is characterized by containing, as an active ingredient, a steryl glucopyranoside represented by general formula (I).

[Chemical Formula 1]

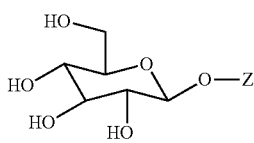

(I)

[Chemical Formula 2]

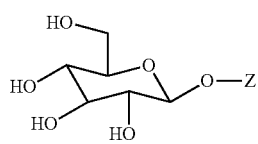

(I)

In the general formula (I), Z represents a sterol residue from which the hydroxyl group attached to the 3-position of a cyclopentanohydrophenanthrene ring has been removed.

As the sterol residue represented by Z, residues of cholesterol, β-sitosterol, stigmasterol, campesterol, and brassicasterol represented by formulae 2 below can be exemplified.

[Chemical Formula 3]

(II)

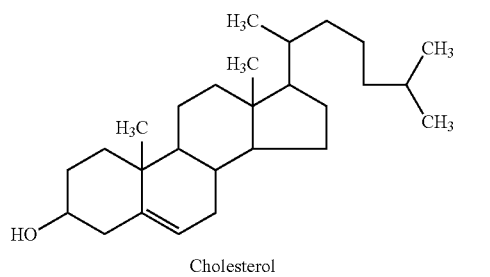
Cholesterol

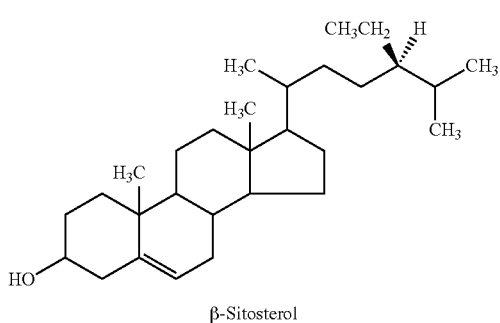
β-Sitosterol

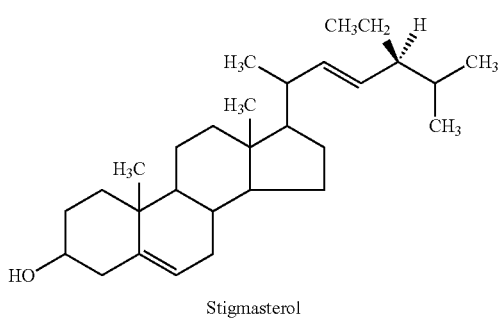
Stigmasterol

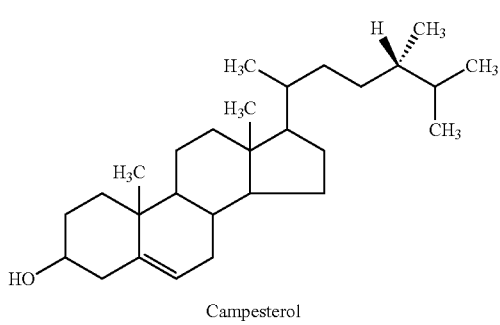
Campesterol

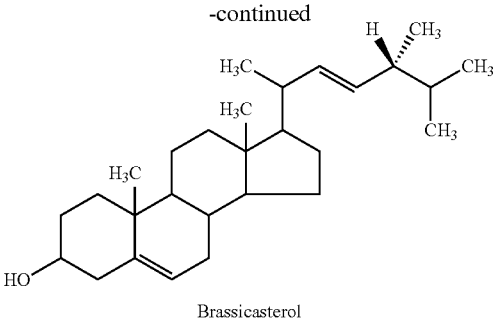
Brassicasterol

The cholesterol is a sterol that is widely distributed in the animal kingdom. The β-sitosterol is a typical plant sterol and usually often exists together with campesterol, stigmasterol, and the like. It is a major sterol in cottonseed oil, tar oil, soybean oil, and the like.

The stigmasterol is abundant in soybean oil, is widely distributed in the plant kingdom, such as in coconut oil and cotton seeds, and often exists together with β-sitosterol and campesterol.

The campesterol is contained in colza seeds, soybean, wheat germs, rapeseed, and the like.

The brassicasterol is contained in seeds of brassicaceous plants, seaweed, shellfish, and the like.

Some of these steryl glucopyranosides have isomers, and any isomers can be used. Furthermore, the glucopyranosyl bond may be in either the α-form or the β-form.

In the present invention, a cholesteryl glucopyranoside is preferable as the steryl glucopyranoside from the viewpoint of hair growth and hair restoration effects.

In the present invention, the steryl glucopyranoside represented by the general formula (I) may be a naturally occurring substance or a synthetic product.

In general, steryl glucopyranosides can be obtained by extraction from natural products or chemical synthesis using a sterol and D-glucose.

As the cholesteryl glucopyranoside, which is preferable in the present invention, a synthetic product may be used.

As the naturally occurring substance, for example, a substance obtained from bird feathers can be preferably used.

The steryl glucopyranoside represented by the general formula (I) can be synthesized in the following manner.

[Synthesis Method of Steryl Glucopyranoside]

In an appropriate solvent, any of various sterols and an acetohalogeno-α-D-glucopyranose are reacted at a temperature of nearly room temperature in the presence of a catalyst, such as mercury cyanide or silver oxide, to give tetraacetyl steryl-β-D-glucopyranoside, followed by purification by silica gel column chromatography.

Next, the purified tetraacetyl steryl-β-D-glucopyranoside is, for example, subjected to hydrolysis treatment in a methanol-water solvent at a temperature of nearly room temperature to give an objective steryl-β-D-glucopyranoside.

When a steryl-α-D-glucopyranoside is synthesized, in the method described above, instead of the acetohalogeno-α-D-glucopyranose which is a starting material, an acetohalogeno-β-D-glucopyranose is used.

Furthermore, for example, a cholesteryl glucopyranoside or the like can be obtained from bird feathers by the method described below.

[Naturally Occurring Cholesteryl Glucopyranoside]

Bird feathers are crushed and treated with an appropriate extracting solvent to first extract total lipids.

Subsequently, the portion dissolved in methanol-water is separated from the total lipids, and then is subjected to weak alkali treatment to obtain alkali-stable complex lipid fraction.

The resulting compound lipid fraction is subjected to silicic acid column chromatography or silicic acid thin layer chromatography (silicic acid TLC) to give a crude cholesteryl glucopyranoside. By further subjecting the resulting crude product to silicic acid TLC, a purified cholesteryl glucopyranoside is obtained.

The hair growth and hair restoration material according to the present invention contains a steryl glucopyranoside represented by the general formula (I), and has an excellent feature in that even at an extremely dilute concentration of $10^{-13}$ or $10^{-12}$ g/mL, hair growth and hair restoration effects are exhibited.

Note that, even if the content is increased, hair growth and hair restoration effects are not obtained in proportion to the increase of the amount, but a tendency is recognized in which the hair growth and hair restoration effects are rather decreased.

Therefore, the content of the steryl glucopyranoside is preferably $10^{-13}$ to $10^{-8}$ g/mL, and more preferably $10^{-13}$ to $10^{-9}$ g/mL.

Examples of the dosage form of the hair growth and hair restoration material of the present invention include, but not particularly limited to, a hair tonic, a shampoo, a rinse, a pomade, a hair lotion, a hair cream, a hair treatment agent, and the like, which are usually used as a hair growth and hair restoration material.

These hair growth and hair restoration materials can be prepared by the same method as that for usual hair growth and hair restoration materials except that the steryl glucopyranoside represented by general formula (I) is mixed thereinto.

Furthermore, the hair growth and hair restoration material according to the present invention is prepared by mixing additives, which are normally used for hair growth and hair restoration materials and which are appropriately selected, such as hydrocarbons, waxes, oils and fats, esters, a higher fatty acid, a higher alcohol, a surfactant, a perfume, a pigment, an antiseptic, an antioxidant, an ultraviolet protective agent, alcohols, a pH adjuster, and various medicinal properties for different purposes.

Furthermore, hair growth and hair restoration components other than the steryl glucopyranoside, which is the hair growth and hair restoration component of the present invention, can be used in combination with the steryl glucopyranoside. Examples thereof include estrogenic hormones, a peripheral blood flow promoter, a local stimulant, a keratolytic drug, an antiseborrheic drug, a germicidal agent, a metabolic activator, an active oxygen inhibitor, an antiphlogistic agent, a nutrient, and, a moisturizer.

EXAMPLES

The hair growth and hair restoration material according to the present invention will be described in detail below on the basis of Examples. It is to be understood that the present invention is not limited to these examples.

Production Example 1

A cholesteryl glucopyranoside derived from chicken feathers (hereinafter, abbreviated as "FCG") was obtained in the following manner.

1) Extraction of Total Lipids

Chloroform-methanol (volume ratio 2:1) (6 L) was added to 350 g of crushed chicken feathers, followed by shaking for 2 hours.

After suction filtration was performed, 6 L of chloroform-methanol (volume ratio 2:1) was further added to the residue, followed by shaking for 2 hours.

After suction filtration was performed, 6 L of chloroform-methanol (volume ratio 1:2) was further added, followed by shaking for 2 hours to extract lipids.

The resulting total extracts were concentrated, dried, and partitioned with chloroform-methanol-water (volume ratio 8:4:3). Then, the lower layer was concentrated and dried to obtain 5.6 g of total lipids.

2) Preparation of Alkali-Stable Complex Lipid Fraction

Hexane (900 mL) and methanol (1,800 mL) were added to the total lipids obtained in 1) described above, followed by stirring.

Then, 300 mL of water was added thereto, and stirring was performed again. The lower methanol-water layer was separated.

Methanol (600 mL) was added again to the upper hexane layer, followed by stirring. Then, 150 mL of water was added thereto, followed by stirring. The lower layer was separated.

The methanol-water layers were combined, concentrated, and dried. Then, weak alkali treatment (resolved at a temperature of 37° C. for 2 hours in a 0.4 mol/L methanolic KOH solution) was performed.

3) Isolation of FCG by Silicic Acid Column Chromatography and Silicic Acid Thin Layer Chromatography The alkali-stable complex lipid fraction obtained in 2) described above was separated into chloroform-acetone (volume ratio 7:3) soluble and insoluble portions, and each portion was subjected to silicic acid column chromatography.

The soluble portion was eluted with chloroform-acetone (volume ratio 7:3) 500 ml, chloroform-acetone (volume ratio 1:1) 500 mL (fraction 1), acetone 500 mL (fraction 2), and chloroform-methanol (volume ratio 2:1) 500 mL.

The insoluble portion was eluted with chloroform-acetone (volume ratio 1:1) 650 mL (fraction 3), acetone 300 mL (fraction 4), and chloroform-methanol (volume ratio 2:1) 300 mL.

Each of the fractions was subjected to silicic acid TLC (silicic acid thin layer chromatography) using chloroform-methanol-water (volume ratio 65:16:2) as a developing solvent, and the spot of cholesteryl glucopyranoside (CG) was confirmed.

The fraction 1 and a combination of the fractions 2 and 4 were subjected to silicic acid. TLC using chloroform-methanol (volume ratio 95:12) as a developing solvent, and the CS spots were separated.

26.7 mg and 12.7 mg of crude CS were obtained.

The fraction 3 was further subjected to silicic acid column chromatography, and eluted with chloroform-acetone (volume ratio 7:3) 500 mL, chloroform-acetone (volume ratio 1:1) 500 mL (fraction 5), and acetone 500 mL.

From the fraction 5, 12.0 mg of crude CS was obtained.

The crude CG portions were combined and subjected to silicic acid TLC using chloroform-methanol (volume ratio 95:12) as a developing solvent, and the CG spot was separated. Thus, 40 mg of purified CG (FCG) was obtained.

Production Example 2

A synthetic cholesteryl glucopyranoside (hereinafter, abbreviated as "SCG") was obtained in the following manner.

Note that the acetobromoglucose, cholesterol, silver oxide, mercury cyanide, and 30% by mass ammonia water used herein were special grade chemicals manufactured by Wako Pure Chemical Industries, Ltd.

1) Synthesis of Tetraacetyl Cholesteryl-β-D-Glucopyranoside Using Mercury Cyanide In a 50-mL eggplant flask, 193 mg of cholesterol and 1.238 g of acetobromo-α-D-glucopyranose were added to 5 mL of $CH_3CN$, and stirring was performed.

$Hg(CN)_2$ (411 mg) was added to the resulting mixture, followed by stirring at room temperature for 3 hours, and the disappearance of acetobromo-α-D-glucopyranose was confirmed by TLC.

$CH_2Cl_2$ (10 mL) was added to the mixture, and suction filtration was performed.

The resulting filtrate was subjected to liquid separation with a saturated $NaHCO_3$ aqueous solution and water. $MgSO_4$ was added thereto, and after the mixture was left to stand for a night, suction filtration and concentration were performed.

The resulting mixture was fractionated with a $SiO_2$ column (Wakogel C-200, developing solvent hexane:ethyl acetate volume ratio=19:1 200 mL, 9:1 100 mL, 4:1 100 mL, 1:1 100 mL) to obtain 252 mg of tetraacetyl cholesteryl-β-D-glucopyranoside (yield 70.4%).

2) Synthesis of Tetraacetyl Cholesteryl-β-D-Glucopyranoside Using Silver Oxide

In a 500-mL eggplant flask, 15.09 g of cholesterol and 30.65 g of acetobromo-α-D-glucopyranose were added to 200 mL of $CH_2Cl_2$, and stirring was performed.

$Ag_2O$ (21.00 g) was added to the resulting mixture, followed, by stirring at room temperature for 3 hours, and 30.65 g of acetobromo-α-D-glucopyranose and 21.00 g of $Ag_2O$ were further added thereto.

After 10 hours, 30.65 g of acetobromo-α-D-glucopyranose and 21.00 g of $Ag_2O$ were further added thereto.

The mixture was stirred for 12 hours, and after the disappearance of acetobromo-α-D-glucopyranose was confirmed by TLC, suction filtration was performed.

The resulting filtrate was concentrated and fractionated with a $SiO_2$ column (Wakogel C-200, developing solvent hexane:ethyl acetate volume ratio=19:1 500 mL, 9:1 500 mL, 4:1 100 mL, 1:1 500 mL).

Furthermore, under the same conditions, $SiO_2$ column was repeated to obtain one spot of tetraacetyl cholesteryl-β-D-glucopyranoside (15.62 g) (yield 55.8%) by TLC.

(3) Conversion of Tetraacetyl Cholesteryl-β-D-Glucopyranoside into Cholesteryl-β-D-Glucopyranoside by Hydrolysis (a) Tetraacetyl cholesteryl-β-D-glucopyranoside (100.2 mg) obtained in 1) was dissolved in 50 mL of methanol.

Furthermore, 10 mL 30% by mass ammonia water was added thereto.

The mixture was stirred at room temperature for 12 hours, and the disappearance of the starting material was confirmed by TLC.

The resulting solution was concentrated to obtain 68.2 mg of cholesteryl-β-D-glucopyranoside (yield 88.9%).

(b) Tetraacetyl cholesteryl-β-D-glucopyranoside (15.41 g) obtained in 2) was dissolved in 300 mL of methanol.

Furthermore, 50 mL of 30% by mass ammonia water was added thereto.

The mixture was stirred at room temperature for 12 hours, and the disappearance of the starting material was confirmed by TLC.

The resulting solution was concentrated to obtain 11.31 g of cholesteryl-β-D-glucopyranoside (yield 95.9%).

This product was recrystallized with ethanol-water to obtain white powder (4.58 g). Furthermore, the mother liquid was crystallized again to obtain light brown powder (2.7 g).

The cholesteryl-β-D-glucopyranoside synthesized by this method was used for an activity test.

<Results of Analysis> i) Confirmation of Structure of Tetraacetyl Cholesteryl-β-D-Glucopyranoside

The result of $^1$H-NMR of the tetraacetyl cholesteryl-β-D-glucopyranoside obtained in each of 1) and 2) showed good agreement with literature data.

Furthermore, generation of tetraacetyl cholesteryl-α-D-glucopyranoside, which is a diastereoisomer, was not observed.

ii) Confirmation of Structure of Cholesteryl-β-D-Glucopyranoside

FIG. 1 shows $^1$H-NMR of the cholesteryl-β-D-glucopyranoside obtained in 3) (b).

Figure 2:
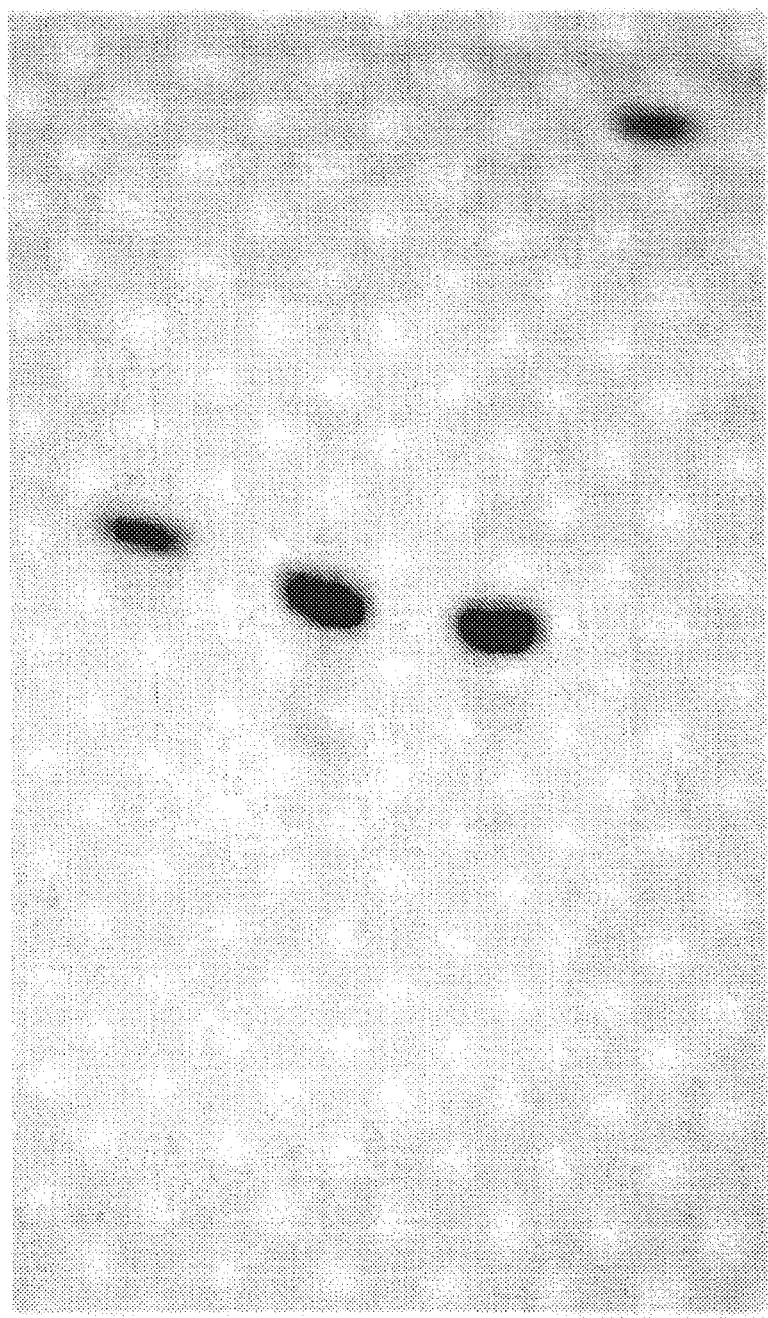
FIG. 2 is a silicic acid TLC chromatogram of cholesteryl-β-D-glucopyranoside (synthetic CG) obtained in Production Example 2-(3) (b).
Figure 3:
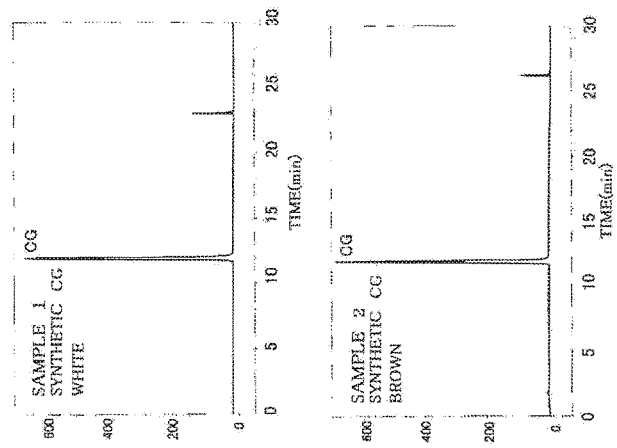
FIG. 3 is a HPLC chromatogram of cholesteryl-β-D-glucopyranoside (synthetic CG) obtained in Production Example 2-(3) (b).

The cholesteryl-β-D-glucopyranoside showed good agreement with literature data. The hydrolysis reaction quantitatively proceeded, iii) Purity of Cholesteryl-β-D-Glucopyranoside A TLC chromatogram and a HPLC chromatogram of the cholesteryl-β-D-glucopyranoside obtained in 3) (b) are shown in FIGS. 2 and 3, respectively.

As is evident from these results, each of the white powder and the light brown powder gives one spot and one peak.

Production Example 3

A steryl glucopyranoside derived from corn (hereinafter, abbreviated as "CSG") was obtained in the following manner.

100 G (raw mass) of corn seeds (sweet corn species) was heated with steam at a temperature of 100° C. for 3 minutes to deactivate enzymes. Then, homogenization was performed with a Polytron-type homogenizer, using 5 volumes of chloroform:methanol (2:1, v/v), and suction filtration was performed.

The residue was subjected to the same treatment using chloroform:methanol (2:1, v/v) and chloroform:methanol (1:2, v/v), and an extract was collected each time.

After the extracts were concentrated, water-soluble components, which were mixed, were removed from the mixture by washing. The lower chloroform layer was subjected to vacuum concentration to obtain total lipids. About 1.7 g of the total lipids was collected.

Then, the total lipids were subjected to silicic acid column chromatography using a chloroform-acetone-methanol system, and fractionated into neutral lipid, glycolipid, and phospholipid components.

The glycolipid fraction was subjected to silicic acid column chromatography using a chloroform-acetone system, and rough fractionation was performed. Then, a steryl glucopyranoside (CSG) was purified with preparative silicic acid TLC using chloroform-methanol-water (65:16:2, v/v) as a developing solvent.

The yield was 3.4 mg per 100 g (raw mass) of corn.

Production Example 4

A steryl glucopyranoside derived from rice (hereinafter, abbreviated as "RSG") was obtained in the following manner.

As in Production Example 3, total lipids were extracted from rice bran. The yield of the total lipids was 10.9 g per 100 g of rice bran.

Next, as in Production Example 3, a steryl glucopyranoside (RSG) was separated from the total lipids and purified. The yield was 26.7 mg per 100 g (raw mass) of rice bran.

Reference Example 1

Preliminary Test for Hair Growth Using Mice

A 70% by mass aqueous ethanol solution containing FCG obtained in Production Example 1 at a concentration of 10 pg/mL (sample solution) was prepared.

The sample solution (20 μL) was applied onto the shaved back skin of four 9-week-old ICR male mice, and skin was collected after 3 hours and after 6 hours.

The skin was subjected to immunostaining for bFGF (basic fibroblast growth factor), Hsp70 (heat shock protein 70), and VEGF (vascular endothelial cell growth factor) by the fluorescent antibody technique and HE staining (hematoxylin-eosin staining), and samples of 14 μm-thick cryostat sections were prepared.

The samples were observed with a microscope and camera (manufactured by Carl Zeiss, Jena Company; AxioCam MRc5-equipped Axioskop).

(1) 3 Hours after Application
<HE Staining>

In one of two mice, local extension of the hair root and enlargement of the hair bulb were observed.

Hair root in anagen: The hair matrix in which the hair root grew was considerably enlarged and came into contact with the hair papilla like a cap. The hair papilla was fully incorporated by the enlarged hair matrix in some hairs.

Furthermore, in the hair follicle (external root sheath) and the epidermis continuous therewith, local stratification and enlargement of the bulge region were observed.

<bFGF Immunostaining>

Strong expression of bFGF was detected in the stratified hair follicle in the vicinity of the epidermis and the stratified epidermis continuous therewith, the enlarged bulge region, the external root sheath in the outermost layer of the hair matrix, erector pili muscles, and the like.

In particular, strong expression of bFGF was induced, in the external root sheath at the surface of the hair matrix in contact with the hair papilla.

<VEGF Immunostaining>

Ethanol control mice: Cells in the epithelium and the slightly enlarged bulge region were positive to VEGF.

FCG-applied mice: VEGF positive reaction was found in hair papilla cells in the hair matrix, and possibly, fibroblasts localized in the outermost layer of the hair matrix.

Expression of VEGF was observed in the epithelium and hair papilla cells of the hair root in telogen.

<Hsp70 Immunostaining>

Weak to moderate expression of Hsp70 was detected in hair papilla cells of the hair root in telogen.

Furthermore, weakly positive reaction was observed in erector pili muscles and fibroblasts, but the bulge region was negative.

(2) 6 Hours after Application
<HE Staining>

Most of the hair roots extended to the subcutaneous tissue, and some of the hair roots were curved in a J-shape.

<bFGF Immunostaining>

Hair bulbs in which the hair papilla was fully incorporated by the hair matrix were observed, but the expression of bFGF in hair papilla cells became weak.

It seems that strong expression of bFGF is transiently induced at the time when hair papilla cells come into contact with the hair matrix and incorporation into the hair matrix starts.

The expression of bFGF in erector pili muscles reduced to moderate.

From the results described above, the following conclusions can be made.

When FCG is applied, expression of bFGF is induced in the epidermis, the external root sheath, the bulge region, the hair matrix, and the like, and cell division is induced in these tissues.

The epidermis of a normal mouse consists of a two-layered cuboidal epithelium. It is believed that the epithelium and the external root sheath continuous therewith are stratified, and probably, the stratification acts on the extension of the hair root and becomes involved in contact with the hair papilla.

In the bulge region, the hair matrix, and the like, enlargement and expression of bFGF are further enhanced by cell division.

The hair root in telogen does not take in the form of a hair matrix. However, formation of the hair matrix in anagen is induced in response to division and proliferation.

The hair papilla cells are divided, proliferated, and enlarged by contact with the hair matrix which is being differentiated, and stronger expression of bFGF occurs.

Along with the formation of the hair matrix, incorporation of the hair papilla starts. When the hair papilla is fully incorporated by the hair matrix, formation of the hair root is completed.

Expression of bFGF becomes slightly weak in the hair papilla in the hair bulb, and instead of this, expression VEGF is induced.

The expression of VEGF suggests induction of microvessels into the hair bulb, and thus differentiation of the anagen hair root is completed.

Examples 1 to 4

1) Preparation of Sample Solutions

The FCG obtained in Production Example 1, the SCG obtained in Production Example 2, the CSG obtained in Production Example 3, and the RSG obtained in Production Example 4 were each dissolved, in 70% by mass ethanol water, and the following solutions were prepared:
FCG 1 pg/mL solution,
FCG 10 pg/mL solution,
FCG 100 pg/mL solution,
SCG 1 pg/mL solution,
SCG 10 pg/mL solution,
SCG 100 pg/mL solution,
CSG 1 pg/mL solution,
CSG 10 pg/mL solution,
RSG 1 pg/mL solution, and
RSG 10 pg/mL solution.

Furthermore, commercially available cholesterol (hereinafter, abbreviated as "Cho") was dissolved in 70% by mass ethanol water to prepare a Cho 10 pg/mL solution.

2) Hair Growth Test

The body hair on the back of 8 to 9-week-old C3H male mice was shaved using an electric clippers for animal use ("Thrive clipper, Model 600AD" manufactured by Daito Electric Company) together with a rotary shaver (National ES611).

Each of the sample solutions (20 μL) was applied in four portions to the skin in central parts of the shaved backs of mice while repeating air drying. The application was conducted 24 hours after shaving.

The hair growth effect was evaluated 2 weeks after the application of the sample solution on the basis of observation with the naked eye and photographs taken by a digital camera. Furthermore, as controls, mice applied with 70% by mass ethanol water and mice not applied with a sample solution were used.

The results are shown in Table 1.

TABLE 1

| | Sample solution | Hair growth state 2 weeks after application |
|---|---|---|
| Example 1 | FCG 1 pg/mL | 6/8 |
| | FCG 10 pg/mL | 4/8 |
| | FCG 100 pg/ml | 5/7 (one mouse died) |
| | Cho 10 pg/mL | 4/8 |
| | 70% by mass ethanol water (control) | 3/8 |
| | Not applied (control) | 3/8 |
| Example 2 | SCG 1 pg/mL | 6/8 |
| | SCG 10 pg/mL | 5/8 |
| | SCG 100 pg/ml | 3/8 |
| | 70% by mass ethanol water (control) | 2/7 (one mouse died) |
| | Not applied (control) | 1/8 to 2/8 |
| Example 3 | CSG 1 pg/mL | 3/8 to 4/8 |
| | CSG 10 pg/mL | 3/8 |
| | 70% by mass ethanol water (control) | 2/8 to 3/8 |
| | Not applied (control) | 0/8 |
| Example 4 | RSG 1 pg/mL | 4/8 |
| | RSG 10 pg/mL | 5/8 |
| | 70% by mass ethanol water (control) | 1/8 |
| | Not applied (control) | 2/8 |

Under the column "hair growth state", 6/8 means that hair growth was observed in 6 out of 8 mice.

The followings are evident from Table 1.

The same hair growth action as that of the cholesteryl glucopyranoside derived from feathers (FCG) is observed in the synthetic cholesteryl glucopyranoside (SCG).

Furthermore, a hair growth action, although weak, is observed in the plant-derived steryl glucopyranosides (CSG and RSG) and cholesterol (Cho).

Furthermore, in FCG and SCG, the hair growth action on mice at a concentration of 1 pg/mL is higher than that at a concentration of 10 pg/mL.

Example 5

The hair growth effect of FCG on head hair of a 46-year-old female was examined.

After hair was thoroughly washed and dried completely with a dryer, about 3.5 mL of a 70% by mass aqueous ethanol solution (sample solution) containing FCG at a concentration of 10 pg/mL was evenly applied, to the scalp once a day.

Before use of the sample solution and 4 months after start of use, photographs were taken by a digital camera from the forehead and the top of head. The results are shown in FIG. 4.

Figure 4:
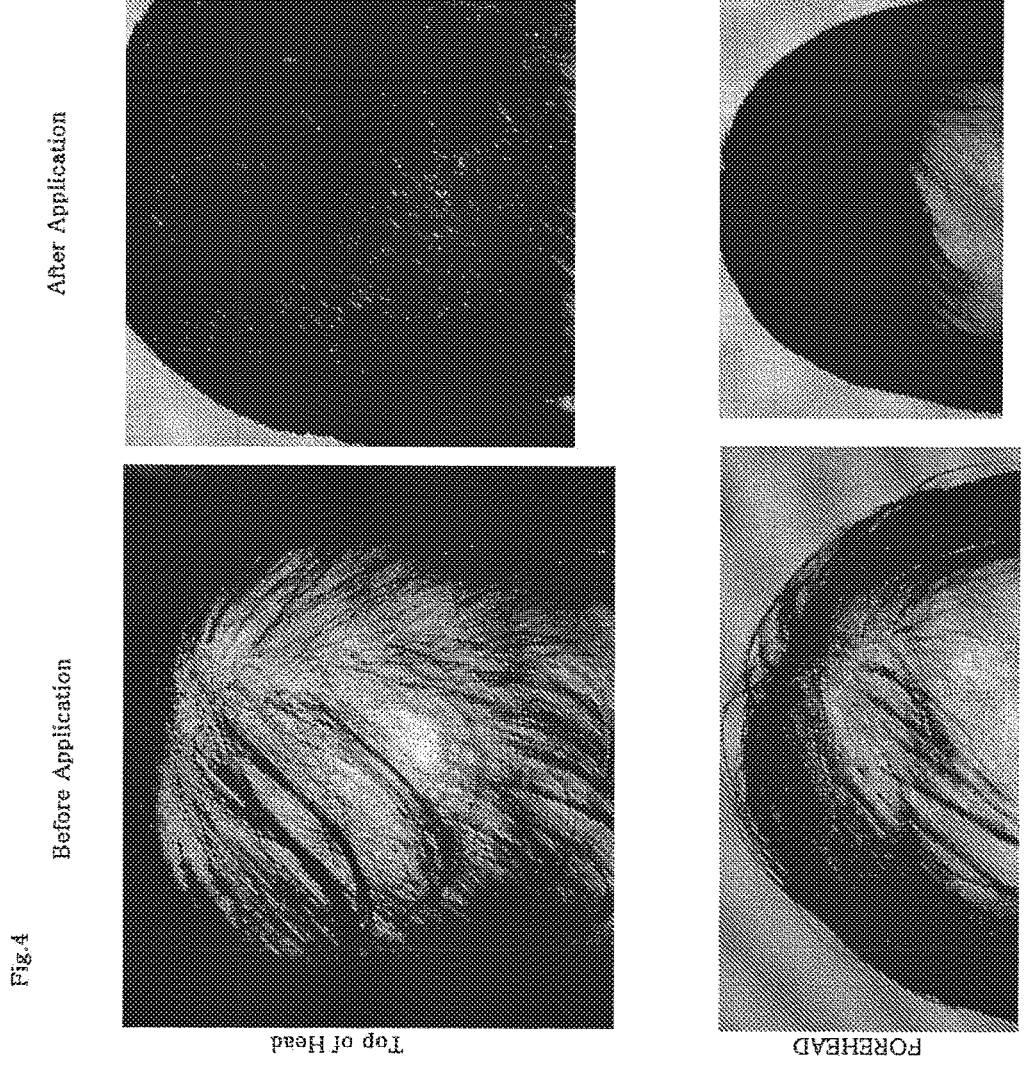
FIG. 4 includes photographs of a head, showing the results of a hair growth test on head hair of a 46-year-old female applied with FCG in Example 5 of the present invention.

As is evident from FIG. 4, 4 months after start of use, a large amount of hair growth was observed in both the forehead and the top of head.

Example 6

The hair growth effect of FCG on head hair of a 35-year-old male was examined.

After hair was thoroughly washed and naturally dried completely, about 3.5 mL of a 70% by mass aqueous ethanol solution (sample solution) containing FCG at a concentration of 10 pg/mL was evenly applied to the scalp once a day.

On the date of start of use of the sample solution and 5 months after start of use, photographs of the forehead and the top of head were taken by a digital camera. The results are shown in FIG. 5.

Five months after start of use, hair growth was observed in the forehead, and a good amount of hair growth was observed in the top of head.

Note that at the point of one year after start of use, side effects are not recognized.

INDUSTRIAL APPLICABILITY

The hair growth and hair restoration material according to the present invention contains, as an active ingredient, a steryl glucopyranoside, preferably a cholesteryl glucopyranoside, and exhibits excellent hair growth and hair restoration effects even when the concentration of the component is extremely dilute (at $10^{-13}$ or $10^{-12}$ g/mL). This hair growth and hair restoration material has a possibility of being widely used as a medical and pharmaceutical product or a cosmetic product.

The invention claimed is:

1. A method for hair growth or hair restoration, the method comprising:
    applying a composition on man or woman to grow or restore hair,
    characterized in that the composition comprises, as an active ingredient, $10^{-13}$ to $10^{-11}$ g/mL of a steryl glucopyranoside represented by general formula (I):

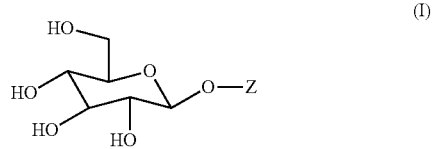

(I)

wherein Z represents a cholesterol residue.

2. The method of claim 1, wherein applying the composition on man or woman includes applying the composition on a scalp of the man or woman to grow or restore hair.

3. The method of claim 1, characterized in that the steryl glucopyranoside is a naturally occurring substance and/or a synthetic product.

4. The method of claim 3, characterized in that the steryl glucopyranoside is obtained from bird feathers.

5. The method of claim 1, characterized in that the composition comprises as the active ingredient $10^{-13}$ to $10^{-12}$ g/mL of the steryl glucopyranoside.

* * * * *